(12) United States Patent
Gombert et al.

(10) Patent No.: US 10,531,930 B2
(45) Date of Patent: Jan. 14, 2020

(54) ROBOTIC SYSTEM

(71) Applicant: ABB GOMTEC GMBH, Seefeld (DE)

(72) Inventors: Bernd Gombert, Wörthsee (DE);
Leopold Bock-Krausen, München (DE)

(73) Assignee: ABB Schweiz AG, Baden (CH)

( * ) Notice: Subject to any disclaimer, the term of this patent is extended or adjusted under 35 U.S.C. 154(b) by 327 days.

(21) Appl. No.: 14/908,166

(22) PCT Filed: Jul. 29, 2014

(86) PCT No.: PCT/EP2014/002066
§ 371 (c)(1),
(2) Date: Jan. 28, 2016

(87) PCT Pub. No.: WO2015/014481
PCT Pub. Date: Feb. 5, 2015

(65) Prior Publication Data
US 2016/0199140 A1    Jul. 14, 2016

(30) Foreign Application Priority Data

Aug. 2, 2013  (DE) .................. 10 2013 012 839

(51) Int. Cl.
*A61B 1/00* (2006.01)
*A61B 1/04* (2006.01)
*A61B 34/32* (2016.01)
*A61B 90/00* (2016.01)

(52) U.S. Cl.
CPC .............. *A61B 34/32* (2016.02); *A61B 90/37* (2016.02); *A61B 2090/3614* (2016.02)

(58) Field of Classification Search
CPC ................... A61B 1/00149; A61B 1/00188
See application file for complete search history.

(56) References Cited

U.S. PATENT DOCUMENTS

| | | | | |
|---|---|---|---|---|
| 5,836,869 A | * | 11/1998 | Kudo ................. | A61B 1/00039 600/102 |
| 2007/0083098 A1 | | 4/2007 | Stern et al. | |
| 2009/0248036 A1 | | 10/2009 | Hoffman et al. | |
| 2012/0016230 A1 | | 1/2012 | Kishima et al. | |
| 2013/0165753 A1 | * | 6/2013 | Takahashi ................ | A61B 1/05 600/109 |
| 2013/0194404 A1 | * | 8/2013 | Christiansen ............ | A61B 1/05 348/67 |
| 2013/0331644 A1 | * | 12/2013 | Pandya .................. | B25J 9/1682 600/102 |

FOREIGN PATENT DOCUMENTS

WO    WO 2012078989    6/2012

OTHER PUBLICATIONS

International Search Report in PCT Application PCT/EP2014/002066, dated Nov. 4, 2014, EPO.

* cited by examiner

*Primary Examiner* — Alexandra L Newton

(57) ABSTRACT

A robot system comprises a base (2), a robot arm (1) connected to the base, a camera (10), at least one objective lens in the camera (10) being movable with the robot arm (1), and a screen (16). A control unit (15) is configured to detect a change in the distance between an object (21) detected by the camera (10) and the objective lens, and to vary the zoom factor of a zoom function of the camera (10) according to the change in distance.

11 Claims, 2 Drawing Sheets

ROBOTIC SYSTEM

TECHNICAL FIELD

The present invention relates to a robotic system, in particular for operating room applications.

BACKGROUND INFORMATION

Robots have been widely used for many years in the field of industrial manufacturing where, thanks to their ability to reproduce pre-programmed sequences of operations within a short time, an infinite number of times, they make possible significant rationalizations in production. Since such robots are in most cases also designed to relieve humans of fatiguing working steps like handling heavy workpieces, they are correspondingly robust in construction and at most can only be deflected slightly through an external impact. Conversely, due to their considerable mass and rapid movements, these robots are quite capable of injuring personnel working in their vicinity. In order to avoid a collision with persons, industrial robots are therefore generally surrounded by a cage when in use.

Robots which are designed for use in the operating theatre cannot, for practical reasons, be shielded by means of a cage, since in general they do not perform an operation on their own; medical personnel are also working on the same patient at the same time. A collision between such a robot and the personnel cannot therefore be prevented with absolute certainty. Since a surgical robot is generally lighter and slimmer in construction than a production robot, in order to avoid unnecessarily blocking the personnel's view of a surgical field, in the event of a collision a deflection of the robotic arm cannot be wholly prevented. If a tool being handled by the robotic arm is also thereby deflected, this could injure the patient.

It is possible to equip a robotic system with appropriate sensors for detecting any impending collision and with a control unit which, when a collision is predicted, controls an evasive movement of the robotic arm in order to avert the impending collision. However, the possibilities for such an evasive movement are limited when the robotic arm is handling a tool on or in the patient's body which may not be moved at will.

It would be ideal if, in such a situation, only a central section of the robotic arm which connects the base with the tool could perform an evasive movement, while the tool itself remained in position. However, the number of degrees of freedom of the robotic arm is generally only as large as is necessary in order to perform the desired movements of the tool. Therefore, there is a not insignificant likelihood that the degrees of freedom of the robotic arm are not sufficient for an evasive movement in which the tool remains immovable. In such a case, an evasive movement can at best be performed in which the resulting movement of the tool is safe for the patient.

If the tool is a camera, in particular an endoscope camera, the problem arises that any movement of the camera changes the image which it provides of its surroundings. Any movement of the camera can therefore lead to a user who is observing the images supplied by the camera on a screen losing sight of an object which is of interest to him. This possibility exists both with a movement of the camera controlled by the user himself as well as when it moves due to the robotic arm being jolted or in connection with an evasive movement of the robotic arm. In the latter two cases the likelihood is, however, particularly high.

Known from WO 2012/078989 A1 is a robotic system with a movable camera on a robotic arm which can be introduced into the body of a patient through a trocar sleeve in order to monitor a tool. A control unit calculates, on the basis of a known aperture angle of the field of view of the camera and known positions of camera and tool, whether the tool lies in the field of view of the camera. If this is not the case, then the camera is moved away from the tool in order to bring the tool into the field of view. If the tool is to be shown larger, the camera is moved towards the tool, insofar as this is possible without losing the tool from the field of view. The monitoring of other objects, in particular of tissue parts of a patient, is not facilitated with this robotic system.

There is therefore a need for a robotic system with a camera in which the likelihood that an observed object is lost from sight through a movement of the camera is reduced.

SUMMARY

In order to satisfy this need, according to one embodiment of the invention, in a robotic system with a base, a robotic arm connected with the base and a camera, wherein at least one lens of the camera can be moved with the robotic arm, a control unit is configured to register a change in the distance between an object captured by the camera and the lens and to vary the zoom factor of a zoom function of the camera according to the change in distance.

This variable zoom function makes it possible to limit changes in the size in which the object is represented on a screen in the event of a movement of the lens along its optical axis and in this way make it easier for a user to recognise the object following the movement of the lens.

Ideally, the control unit should be configured to keep the size of the object on the screen constant independently of distance.

The zoom function can be implemented in that the lens has a focal length which can be adjusted by means of the control unit.

Alternatively, the camera can include an image processing unit which implements the zoom function in that it transforms a raw image recorded by the camera into an output image using a variable scale.

Various objects can be visible in a raw image generated by the camera. It can be the case that a user specifies to the image processing unit one of these objects, which he wishes to be displayed on the screen with distance-independent size. However, if the movement of the lens is attributable to a collision avoiding movement, then the likelihood is high that the user has not selected an object at the decisive moment. Therefore, the control unit is preferably configured to assume the object to be in a plane on which the camera is focused, since it can be assumed that, if the user wishes to follow an object in view of the camera he will focus the camera on this object.

The lens of the camera can be rotatable around its optical axis by the robotic arm. In this case it is practical for the image processing unit to be configured to output a raw image supplied by the camera on the screen rotated in the opposite direction to the rotation of the lens. In this way, a rotation of the lens which can be necessary in connection with an evasive movement of the robotic arm does not affect the image visible on the screen.

It is practical for the control unit to be connected with means for detecting the approach of a foreign body to the robotic arm and configured to control an evasive movement of the robotic arm on detecting such an approach.

The means for detecting the approach can comprise at least one proximity sensor or a camera.

While a camera can preferably be arranged separately from the robotic arm in order to survey it together with an approaching foreign body, proximity sensors are preferably arranged distributed on the robotic arm in order in each case to detect an approach locally. In particular, this makes possible a simple control of the evasive movement, since the individual proximity sensors can in each case be assigned different strategies for evasive movements according to their positioning on the robotic arm.

The control unit can also be connected with a further robotic arm and can be configured, on detecting a convergence of the robotic arms, to control an evasive movement of the robotic arm.

In particular, a movement of the lens in the direction of its optical axis can be considered as an evasive movement.

In such a case, the control unit can be configured to vary the zoom factor if a movement of the lens in the direction of its optical axis is an evasive movement, but not to vary the zoom factor if the movement is caused by an external command, because if the user issues a corresponding command while observing the image on the screen then he expects to be able to recognize and assess the movement of the camera on the basis of the change in the relationship between the sizes of objects represented in the image, and failure of an intuitively anticipated change in size to occur can leave the user uncertain whether or not the robotic arm has performed the commanded movement.

However, it can also be practical, on a user interface, to offer the user the option of choosing whether, in the case of a movement of the lens controlled by him, the size of the object should be distance-dependent or fixed. This makes it possible, for example, after precisely examining the object by means of the camera from a close proximity between camera and object, to create space for a tool for manipulating the object without having to relinquish the detailed view of the object on the screen.

The control unit can also be configured to control a rotation of the lens around its optical axis as an evasive movement. Although this would not lead to a change in the size of an object displayed on the screen, the rotation of the image associated with the rotation of the camera can hinder the recognition of the object which is of interest, for which reason the rotation of the image should be at least partially compensated by the image processing unit installed downstream.

In this case the image processing unit can, practically, be configured to rotate the raw image supplied by the camera if a rotation of the camera around the optical axis of the lens is an evasive movement, but not to rotate the raw image if the rotation is caused by an external command.

It is practical for the aforementioned user interface also to be used to generate said external commands.

The camera can in particular be part of an endoscope.

If the optical axis of the lens coincides with the longitudinal axis of the endoscope, then an extraction movement of the endoscope does not generally present any risk of injury to the patient and can therefore be performed in connection with an evasive movement, if necessary. A rotation of the endoscope around its axis is also generally possible without any risk of injury.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
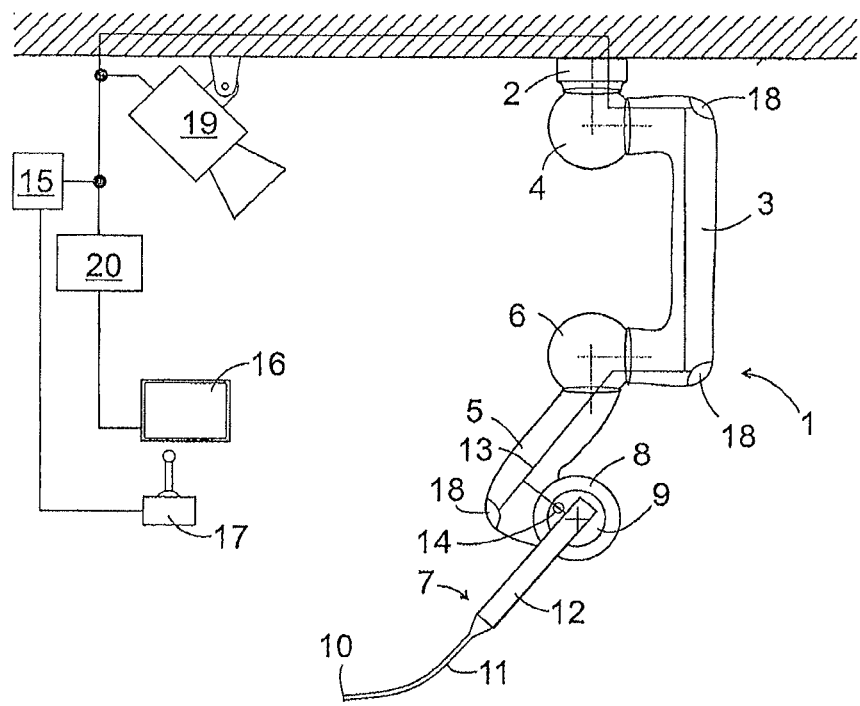
FIG. 1 shows a diagrammatic representation of a robotic system according to a first embodiment of the invention.

FIG. 1 shows, in diagrammatic form, a robotic system according to an embodiment of the present invention. The system comprises a robotic arm 1 with a base 2 mounted in fixed position, in this case for example on the ceiling of an operating room, a first arm section 3, which is connected with the base via a first articulated module 4, a second arm section 5 which is connected with the first arm section 3 via a second articulated module 6, and an endoscope 7 which is detachably attached to a holder 9 connected with the second arm section 5 via the articulated module 8.

The articulated modules 4, 6, 8 are in this case designed as two-axis joints with two shafts arranged orthogonally in relation to one another which are in each case anchored non-rotatingly to an adjacent component of the robotic arm, i.e. the base 2 and the arm section 3 in the case of the module 4, the arm sections 3, 5 in the case of the module 6 and the arm section 5 and the holder 9 in the case of the module 8, and can be rotated with the aid of servomotors housed in the articulated modules 4, 6, 8.

In this case the endoscope 7 comprises a miniaturized camera 10 which is attached to the tip of a flexible insertion tube 11. A base 12 for attachment to the holder 9 can be immovably connected with the insertion tube 11, so that each movement of the camera 10 requires a corresponding movement of the holder 9. However, in order to facilitate the introduction of the endoscope 7 into a lumen of a patient's body, the insertion tube 11 can also be movable with respect to the base 12 and the base 12 can be equipped with servomotors for the longitudinal displacement of the insertion tube 11 or rotation of the insertion tube 11 around its axis.

A data bus 13 extends from a plug connection 14 on the holder 9 via the arm sections 5, 3 and articulated modules 8, 6, 4 of the robotic arm 1 up to a control unit 15 and an image processing unit 20. Although in this case the image processing unit 20 is represented located separately from the endoscope 7, functionally it forms a part of its camera 10. A screen 16 for displaying the images supplied by the camera 10 is connected to the image processing unit 20.

A user interface 17 for controlling movements of the robotic arm 1 or of the endoscope 7 is represented diagrammatically in FIG. 1 as a joystick. The control unit 15 receives positioning commands from a user via the user interface 17 and converts these into actuating commands for the servomotors of the articulated modules 4, 6, 8 as well as, if present, servomotors of the endoscope 7. It can be provided that the control unit 15 queries the endoscope 7 for technical data relating to the endoscope 7, in particular concerning the presence of servomotors and the degrees of freedom of movement of the insertion tube 11 in relation to the base 12, in order if necessary to use the servomotors of the endoscope 7 to drive a movement of the camera 10.

The data bus 13 also connects a plurality of proximity sensors 18 with the control unit 15. In particular, capacitive sensors can be used as proximity sensors 18, since these are capable of detecting the proximity of foreign bodies made of virtually any materials. In this case the proximity sensors 18 are only represented in exposed positions on the arm sections 3, 5; in practice, they can be distributed in larger numbers over the housing of the arm sections 3, 5 in order if necessary not only to register the fact that a foreign body is approaching but, on the basis of a comparison of the signal strengths of differently placed proximity sensors 18, also to make it possible to determine the direction from which the foreign body is approaching, or the point at which it is expected to collide with the robotic arm 1.

Fundamentally, proximity sensors 18 can also be provided on the articulated modules, in particular the articulated modules 6, 8. The articulated module 4 does not require such sensors, since it is connected directly with the fixed-location base 2 and is therefore not capable of evading an approaching foreign body; however, a collision of a foreign body with the articulated module 4 also would not lead to a deflection of the robotic arm 1.

For reasons of efficiency of manufacture and maintenance it can be desirable for all the articulated modules 4, 6, 8 to be of identical design. In such a case, in order to make it possible also to detect the approach of a foreign body to the articulated modules 6, 8 without needing to equip these themselves with sensors, it can be practical to provide proximity sensors on the ends of the arm sections 3, 5 adjacent to the articulated modules 6, 8.

In order to assist the proximity sensors 13 or as a substitute for these, one or more cameras 19 can be provided which are pointed at the robotic arm 1, the images from these being analysed by the control unit 15 in order to recognise the approach of a foreign body to the robotic arm 1.

Figure 2:
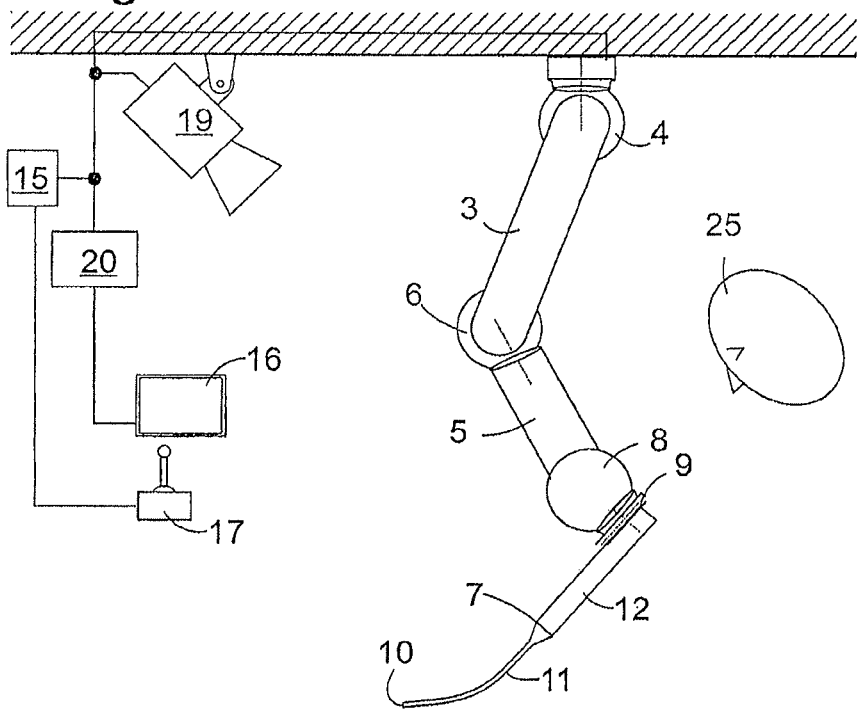
FIG. 2 shows the robotic system from FIG. 1 following an evasive movement.

FIG. 2 shows a typical application situation of the robotic system according to the invention. The endoscope 7 is placed within the body of patient, not shown in the figure, and a surgeon bends his head over the patient in order to have an unobstructed view of a surgical field. If, in this situation, the robotic arm 1 was in the position shown in FIG. 1, the surgeon's head 25 could collide with the arm section 3. This proximity is registered by the control unit 15 by means of the proximity sensors 18 and/or the camera 19. The arm section 3 is moved out of the area in which there is a danger of collision through a rotation of the articulated module 4 around its vertical shaft fixed to the base 2. In the configuration shown in FIG. 2, the arm sections 3, 5 are rotated by approx. 90 degrees in relation to the configuration shown in FIG. 1, so that a central part of the roughly u-formed arm section 3 and the articulated module 8 at the end of the arm section 5 face the viewer. In order to keep the position of the endoscope 7 unchanged during this rotation, the holder 9 is rotated from the position shown in FIG. 1, extending from the articulated module 8 towards the viewer, into a position extending diagonally downwards, and the articulated module 8 is raised through increased angling of the arm sections 3, 5 in relation to the vertical. Although the position of the endoscope 7 remains unchanged as a result, it is rotated around the longitudinal axis of its base 12 or, due to the flexibility of the insertion tube 11, around the optical axis of the camera 10.

Figure 3:
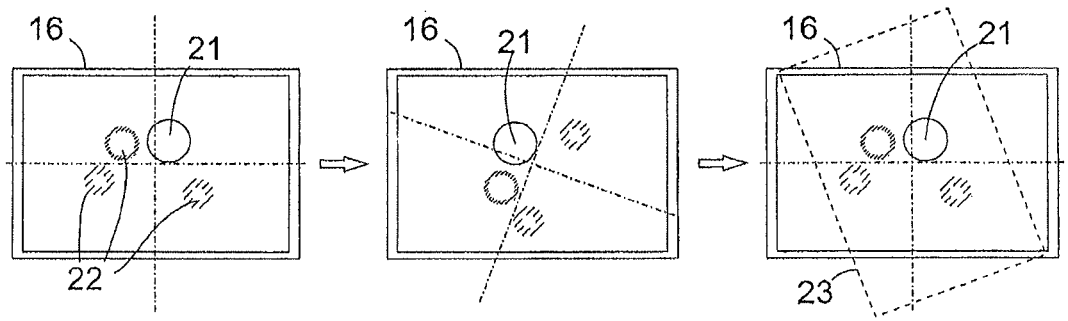
FIG. 3 shows steps of the image processing in a control unit of the robotic system from FIG. 1.

The effect of such a rotation on an image supplied by the camera 10 is illustrated in FIG. 3. The camera 10 supplies a raw image to the image processing unit 20 which, in the configuration shown in FIG. 1, before the evasive movement of the robotic arm 1, is output to the screen 16 untransformed by the image processing unit 20 and contains representations of several objects 21, 22 located in front of the lens 24. A diagrammatic view of the screen 16, on which the objects 21, 22 can be seen, is shown in the left-hand part of FIG. 3. The camera is focused on the object 21, the objects 22 lie outside of a focused plane and therefore appear in the image more or less out of focus.

The rotation of the camera 10 around its optical axis during the course of the evasive movement causes the images of the objects 21 on the sensor chip of the camera 10 also to rotate around the optical axis, so that the raw image supplied by the camera 10 to the image processing unit 20 assumes, for example, the form shown in the center part of FIG. 3.

Since the control unit 15 knows all of the movements performed during the course of the evasive movement of the robotic arm 1, it is able to calculate the rotation of the camera 10 resulting from the evasive movement and to supply a corresponding angle of rotation to the image processing unit 20, on the basis of which the image processing unit 20 calculates a transformed image in which this rotation is reversed. This transformed image 23 is represented in the right-hand part of FIG. 3 as a rectangle outlined in a broken line. In the transformed image 23 the objects 21 have the same position as before the evasive movement and remain visible. If an object 21 has been successfully located within the patient's body, it is thus not lost again as a result of the evasive movement, and the surgeon is not irritated by a rotating movement of the image visible on the screen 16.

A corresponding image transformation can also be carried out by the image processing unit 20 in the case that the user commands, on the user interface 17, a translation movement of the camera 10 but, due to limitations in the freedom of movement of the robotic arm 1, this can only be realized simultaneously with a rotation—not commanded by the user and therefore also not expected—of the camera 10 around its optical axis.

If, in contrast, the user commands, on the user interface 17, a rotation of the camera 10, then he also expects to see this on the screen. In this case the control unit 15 can actually control a physical rotation of the camera 10, without the image processing unit 20 compensating the rotation, or the rotation can be effected purely arithmetically in the image processing unit 20, without the camera 10 being physically rotated.

In a variant of the invention, the camera has a sensor chip which is mounted in the camera such that it can rotate around the optical axis of the lens. In this case no image transformation in the image processing unit 20 is necessary. Instead, the sensor chip is adjusted rotationally around the optical axis, contrary to the rotation of the camera, so that the rotational orientation of the sensor chip remains unchanged in relation to the image which is to be recorded.

Figure 4:
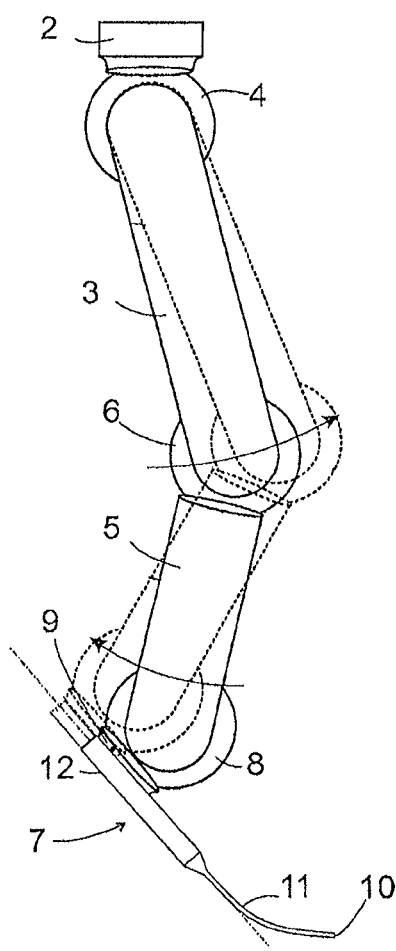
FIG. 4 shows the robotic system performing a second evasive movement.

FIG. 4 shows another evasive movement of the robotic arm. In this case the robotic arm 1 is initially in a position represented with solid lines and evades a foreign body approaching from the left at approximately the height of the articulated module 6 through transition into the position represented with broken lines. This evasive movement does not involve any rotation of the endoscope 7 around its optical axis, instead it involves a movement withdrawing its camera 10 from the patient's body.

Figure 5:
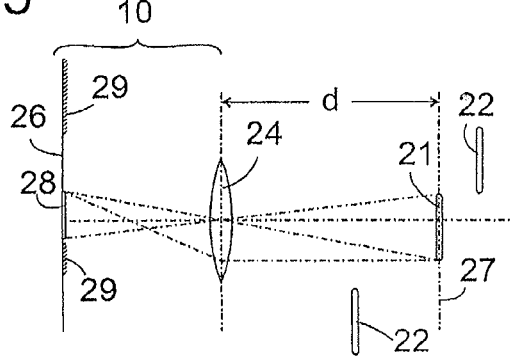
FIG. 5 shows a diagrammatic representation of the lens and sensor chip of an endoscope camera of the robotic system before the evasive movement shown in FIG. 4.

FIG. 5 shows, in diagrammatic form, a lens 24 and a sensor chip 26 of the camera 10 before the evasive movement. Several objects 21, 22 are located before the lens 24 of the camera 10. The object 21 is located in a plane 27 on which the lens 24 is focused, i.e. it is imaged in sharp focus on the sensor chip 26. The focusing of the lens 24 is controlled by the control unit 15 on the basis of commands issued by the user on the user interface 17, therefore the distance d between the lens 24 and the plane 27 is known to the control unit 15.

Figure 6:
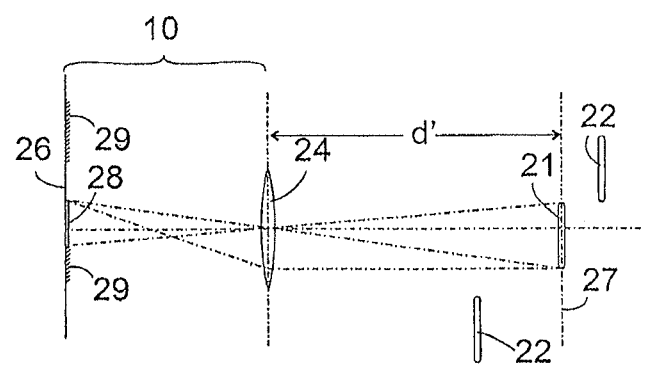
FIG. 6 shows a representation analogous to FIG. 5 following the evasive movement.

During the course of the evasive movement, the distance between the object 21 and lens 24 increases to d', as shown in FIG. 6. The control unit 15 increases the focal length of the lens 24 by the factor d'/d and the distance between lens 24 and sensor chip 26, so that the plane 27 remains imaged in sharp focus on the sensor chip 26 and at the same time the size of the image 28 of the focused object 21 on the sensor chip 26 does not change. Although the position and sizes of images 29 of the other objects 22 change all the more the further distant these are from the plane 27, this has only little influence on the image supplied by the camera 10, since these objects 22 are only projected onto the sensor chip 26 out of focus. The object 21 thus remains clearly recognizable following the evasive movement.

According to an alternative embodiment, in the event of an evasive movement of the camera 10 the control unit 15 only adjusts the focusing of the lens 24, not its focal length. In this case too, the image 28 of the object 21 remains in sharp focus, but its size is changed. In order nonetheless to be able to display the object 21 in unchanged size on the screen 16, the image processing unit 20 enlarges a section of the raw image digitally.

Both embodiments can be combined together, for example such that the control unit 15 switches over to digital enlargement of the raw image if the focal length of the lens 24 has reached its maximum.

If the camera 10, controlled by user commands, is moved along its optical axis, the image correction described above should generally not take place, since in this case the user also expects to see a changed image on the screen in reaction to a movement of the camera 10. Nonetheless, the user can be given the option of selecting on the user interface 17 whether or not he wishes for the image correction to take place in the case of a movement of the camera 10 controlled by him; for example the possibility can be provided that the user can first inspect an object 21 which is to be operated on with the camera 10 from such a close distance that there is hardly space for the foreign bodies 22 obstructing the view between lens 24 and object 21, and then increase the distance while maintaining the image size, in order to create space for a surgical tool between lens 24 and object 21.

REFERENCE NUMBERS 1 robotic arm
2 base
3 arm section
4 articulated module
5 arm section
6 articulated module
7 endoscope
8 articulated module
9 holder
10 camera
11 insertion tube
12 base
13 data bus
14 plug connection
15 control unit
16 screen
17 user interface
18 proximity sensor
19 camera
20 image processing unit
21 object
22 object
23 transformed image
24 lens
25 head
26 sensor chip
27 plane
28 image
29 image Modifications and substitutions by one of ordinary skill in the art are considered to be within the scope of the present invention, which is not to be limited except by the allowed claims and their legal equivalents.

The invention claimed is:

1. A robotic system comprising:
a base (2);
at least a first robotic arm (1) connected with the base;
an imaging camera (10), coupled to said robotic arm, and configured for providing images, wherein at least a lens (24) of the imaging camera (10) can be moved with the at least a first robotic arm (1);
a display screen (16), configured for displaying the images supplied by said imaging camera (10);
a user interface (17), for generating external commands for controlling movement of said at least a robotic arm (1);
at least one of a proximity sensor (18) and a proximity detecting camera (19), for detecting the approach of a foreign body (25) in a vicinity of the at least a first robotic arm (1), and
a control unit (15), coupled to said at least a first robotic arm (1), to said user interface (17), to said at least one of a proximity sensor (18) and a proximity detecting camera (19) and to said display screen (16), and configured to control a zoom factor of a zoom function of the imaging camera (10), and to control movements of the at least a first robotic arm (1) based on said external commands without varying said zoom factor of said zoom function of the camera (10), and wherein the control unit (15) is responsive to said at least one of a proximity sensor (18) and a proximity detecting camera (19), for detecting the approach of a foreign body (25), and responsive to said detecting the approach of a foreign body (25) in a vicinity or the at least a first robotic arm (1), and without reference to said user interface generated external commands, for controlling an evasive movement of the at least a first robotic arm (1) in which the lens (24) is moved in the direction of its optical axis, and to register a change in a distance (d) between an object (21) captured by the imaging camera (10) and the lens (24) and to vary the zoom factor of the imaging camera (10) according to the change in distance (d) so as to keep the size of the object (21) in an image output by the imaging camera (10) constant independent of the distance (d) between the lens (24) and the object (21) and without a user interface generated external commands.

2. The robotic system according to claim 1, characterised in that the lens (24) has a focal length which can be adjusted by the control unit (15).

3. The robotic system according to claim 1, characterised in that the imaging camera (10) includes an image processing unit (20) which is configured to output a raw image recorded by the imaging camera (10) with variable scale.

4. The robotic system according to claim 1, characterised in that the control unit (15) is configured to select the object (21) in a plane (27) on which the imaging camera (10) is focused.

5. The robotic system according to claim 1, characterised in that the lens (24) is rotatable around its optical axis by the robotic arm (1) and wherein an image processing unit (20) is coupled to the imaging camera (10) and configured to output a raw image (23) supplied by the imaging camera (10) that is rotated in an opposite direction to rotation of the lens (24).

6. The robotic system according to claim 1, characterised in that the control unit (15) is connected with a second robotic arm and is configured, on detecting a convergence of the at least a first and the second robotic arms, to control an evasive movement of at least one of the at least a first and the second robotic arm.

7. The robotic system according to claim 1, characterised in that the control unit (15) is configured to vary the zoom factor of the imaging camera (10) if a movement of the lens (24) in the direction of its optical axis is an evasive movement, and not to vary the zoom factor if the movement of the lens (24) in the direction of its optical axis is caused through an external command.

8. The robotic system according to claim 1, characterised in that the control unit (15) is configured to control a rotation of the lens (24) around its optical axis as an evasive movement.

9. The robotic system according to claim 5, characterised in that the image processing unit (20) is configured to rotate the raw image (23) if a rotation of the imaging camera (10) around the optical axis of the lens (24) is an evasive movement, and not to rotate the raw image (23) if the rotation of the imaging camera (10) around the optical axis of the lens (24) is caused through an external command.

10. The robotic system according to claim 1, characterised in that the imaging camera (10) is part of an endoscope (7).

11. The robotic system according to claim 10, characterised in that the optical axis of the lens (24) coincides with a longitudinal axis of the endoscope (7).

* * * * *